United States Patent
Ekwall et al.

(10) Patent No.: US 6,264,606 B1
(45) Date of Patent: Jul. 24, 2001

(54) ISCHEMIA DETECTOR

(75) Inventors: Christer Ekwall, Spånga; Kjell Norén, Solna, both of (SE)

(73) Assignee: Pacesetter AB, Jäfälla (SE)

( * ) Notice: Subject to any disclaimer, the term of this patent is extended or adjusted under 35 U.S.C. 154(b) by 0 days.

(21) Appl. No.: 09/355,683

(22) PCT Filed: Feb. 5, 1998

(86) PCT No.: PCT/SE98/00203

§ 371 Date: Sep. 22, 1999

§ 102(e) Date: Sep. 22, 1999

(87) PCT Pub. No.: WO98/34537

PCT Pub. Date: Aug. 13, 1998

(30) Foreign Application Priority Data

Feb. 7, 1997 (SE) .................................. 9700427

(51) Int. Cl.[7] ...................................... A61B 5/00
(52) U.S. Cl. ................ 600/300; 600/301; 600/484; 600/529; 600/534; 607/19; 607/20
(58) Field of Search .................. 607/3, 5, 17, 19, 607/20; 600/529–538, 300, 301, 484

(56) References Cited

U.S. PATENT DOCUMENTS

| 4,821,735 | 4/1989 | Goor et al. |
| 5,025,786 | 6/1991 | Siegal . |
| 5,156,148 | 10/1992 | Cohen . |
| 5,199,428 | 4/1993 | Obel et al. |
| 5,497,780 | 3/1996 | Zehender . |
| 5,515,859 | * 5/1996 | Paz ...................................... 600/538 |
| 5,833,713 | * 11/1998 | Moberg ................... 607/19 |
| 6,024,705 | * 2/2000 | Schlager et al. .................... 600/508 |

* cited by examiner

*Primary Examiner*—Robert L. Nasser, Jr.
(74) *Attorney, Agent, or Firm*—Schiff Hardin & Waite

(57) ABSTRACT

An ischemia detector has a patient workload sensor and a patient breathing sensor which emits a signal representing sensed workload, and a patient breathing sensor which emits a signal representing sensed breathing activity of a patient. These signals are supplied to a detector unit which identifies a state of ischemia upon an occurrence of a predetermined relation between the sensed workload and the sensed breathing activity. This predetermined relation is a sensed low workload and a simultaneously sensed high breathing activity.

20 Claims, 3 Drawing Sheets

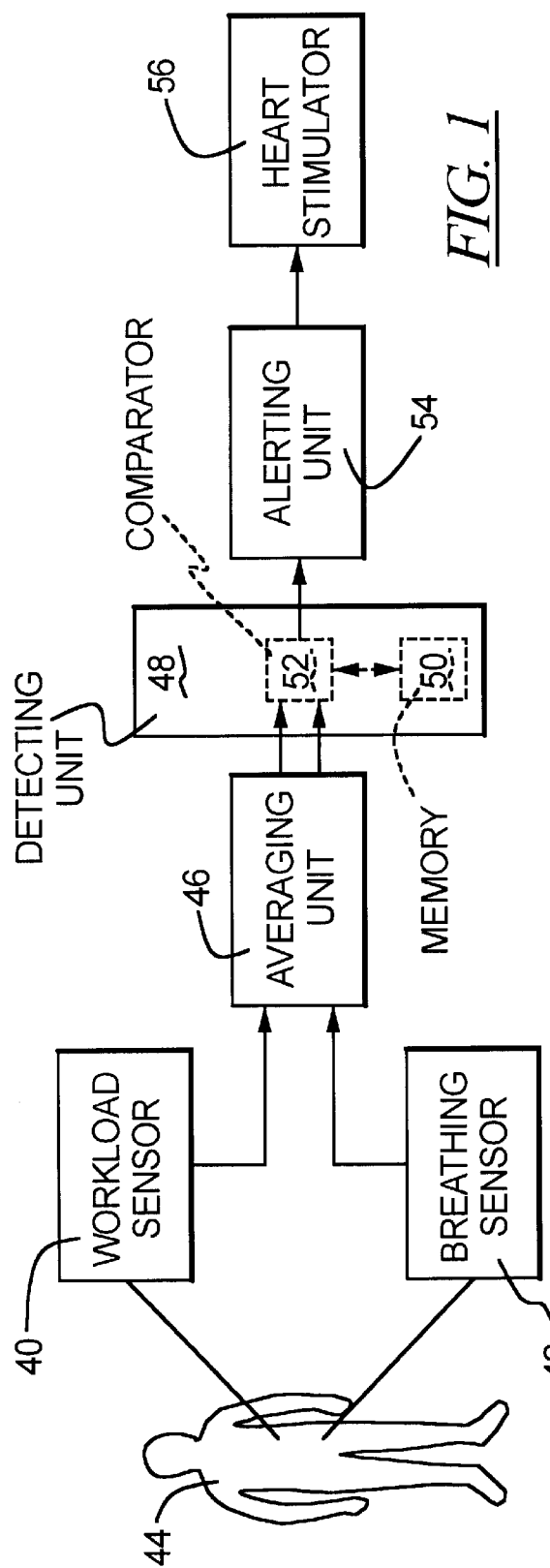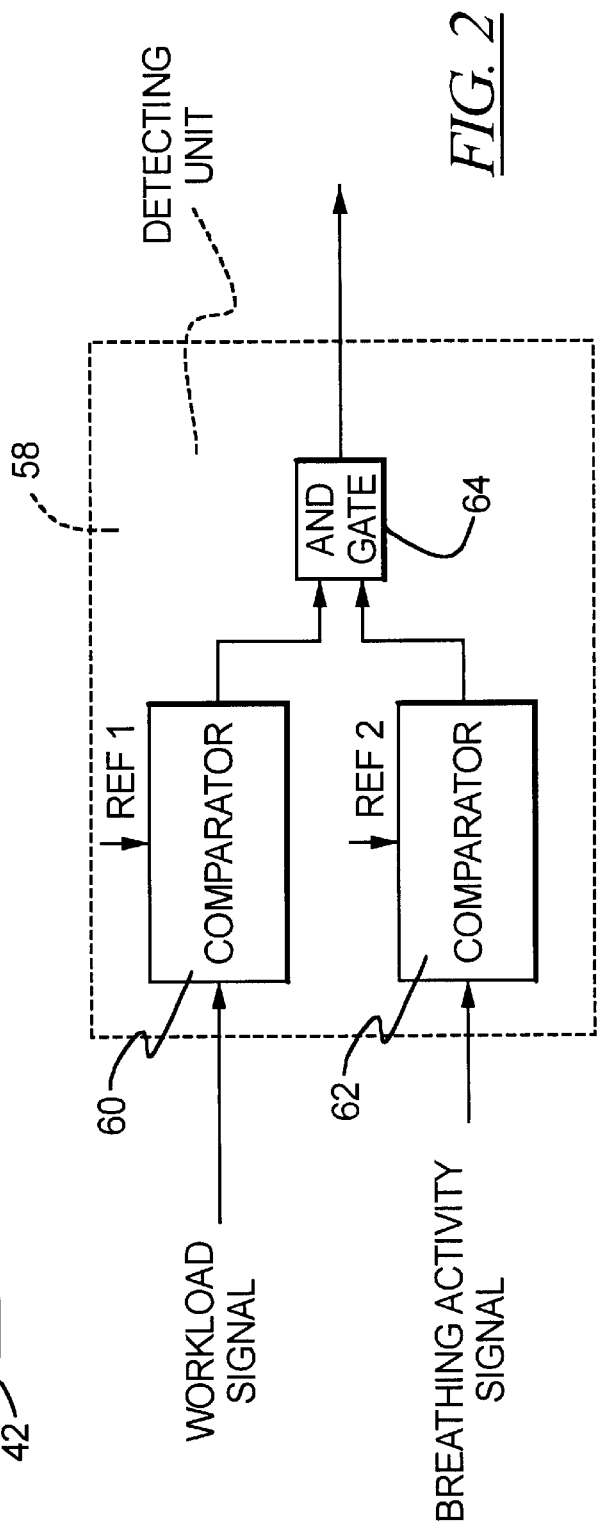

ISCHEMIA DETECTOR

BACKGROUND OF THE INVENTION

1. Field of the Invention

The present invention relates to an ischemia detector and to an implantable heart stimulator having such an ischemia detector.

2. Description of the Prior Art

The blood flow and penetration in the circulatory system of a living subject are dependent on the arterial muscular tension, the so called tonus. Thus the blood flow is controlled by the tonus, the driving force of the flow is the blood-pressure in the elastic aorta and the pressure in the aorta is maintained by the pumping action of the heart. For this pumping action the heart needs energy in the form of oxygen and glucose. About 60% of the oxygen in the heart interstitial fluid is consumed within one heart beat. If the energy supplied to the heart is disturbed the heart contractibility and the pumping action of the heart are severely deteriorated and an oxygen shortage or ischemic situation will rapidly develop. Ischemia results from insufficient blood flow through the heart muscle. Due to blocking or passage congestion of coronary blood vessels of the heart. I ischemia is experienced by the patient as a severe chest pain and is one of the most stressing factors known to the organism. Several techniques for detecting ischemia are known. In U.S. Pat. No. 5,156,148 a system for treating a malfunctioning heart, e.g. ischemia, is known using the variation of selected physiologic parameters. In U.S. Pat. No. 4,821,735 a method and an apparatus for detecting myocardial ischemia are described, wherein the systemic vascular resistance (SVR) in a subject is monitored and the presence of myocardial ischemia is detected when the SVR increases by at least 60% over a base line value.

In U.S. Pat. No. 5,497,780 an apparatus is described for determining an ischemia by measurements of electric potentials between at least three implanted measuring electrodes, two of these electrodes being implanted with their poles in the heart and the third electrode being implanted with its pole lying outside the heart.

In U.S. Pat. No. 5,199,428 a technique is described for detecting ischemia and effecting stimulation of nerves regulating blood pressure and heart rate to reduce the heart's oxygen requirements while providing pacing therapies to maintain the patient's heart rate within acceptable limits to avoid bradyarrhythmias and/or unphysiological AV delays induced by the nerve stimulation. The ischemia detection is based on the occurrence of changes in the ST-segment variation different from pre-determined or programmed threshold levels, or on changes in the pH and/or in the dissolved blood oxygen in venous return blood in the coronary sinus region of the patient's heart.

An ischemic state can also be detected by analysis of recorded IECG's or surface ECG's to determine the heart rate variability. Ischemia can be detected by a lead bend sensor located at the distal end portion of an implanted heart stimulator lead. As the heart wall is thickening and stiffening as the result of an ischemic state, the accompanying change in the moving pattern of the heart wall can be detected in this way. Also sound absorption is affected by changes in the stiffness of the heart tissue and by measuring the absorption of sound waves, generated e.g. at the heart valve closure, on their way from the upper portion of the ventricle to the apex region, an ischemic situation can be detected. Ischemia deteriorates the efficiency of the heart's pumping and an ischemic situation can therefore be detected by studying blood pressures and cardiac outputs, too. Thus, by measuring the difference between the systolic and diastolic pressures and comparing this difference obtained from one heartbeat to the difference obtained from the next heartbeat an ischemic can be detected. An ischemic state can be detected using a flow sensor for measuring cardiac output, as well.

As mentioned above an ischemic state is normally associated with severe pain forcing the patient to sit down or lie down with a reduced heart rate as a consequence. At the same time the patient feels a need for forced breathing, so called hyperventilation.

SUMMARY OF THE INVENTION

It is an object of the present invention to provide an ischemia detector the functioning of which is based on the above mentioned needs of a patient experiencing ischemia.

The above object is achieved in accordance with the principles of the present invention in an ischemia detector having a patient workload sensor and a patient breathing sensor, which respectively emit signals which are supplied to a detector unit, the detector unit detecting a state of ischemia dependent on the occurrence of a predetermined relation between the sensed workload and the sensed breathing activity, this predetermined relation being a sensed low workload and a simultaneously sensed high breathing activity.

For a healthy person the need of an increased respiration rate normally results from an increased effort or workload of the person. The ischemia detector according to the invention is based on the occurrence of the abnormal combination of low workload and high breathing activity, which is typical of ischemic patients.

In an advantageous embodiment of the ischemia detector according to the invention an averaging unit is connected to the workload sensor and breathing sensor which forms average values during time periods of pre-determined lengths of workload and breathing activity respectively, and delivers corresponding average signals to said detector unit. In this way false detections due to accidental variations of transitory nature in the workload and breathing activity are avoided.

In another embodiment of the detector according to the invention an alerting unit is activated in response to a detected ischemia.

According to another aspect of the invention an implantable heart stimulator has means for varying the stimulation rate and an ischemia detector as defined above.

The heart stimulator can have a control unit connected to the ischemia detector for controlling the stimulation rate varying means to lower the stimulation rate in response to the detection of an ischemia.

DESCRIPTION OF THE DRAWINGS

FIG. 1 is a generalized block diagram of an ischemia detector according to the invention.

FIG. 2 is a block diagram illustrating details of an embodiment of the ischemic detector according to the invention.

DESCRIPTION OF THE PREFERRED EMBODIMENTS

Figure 3:
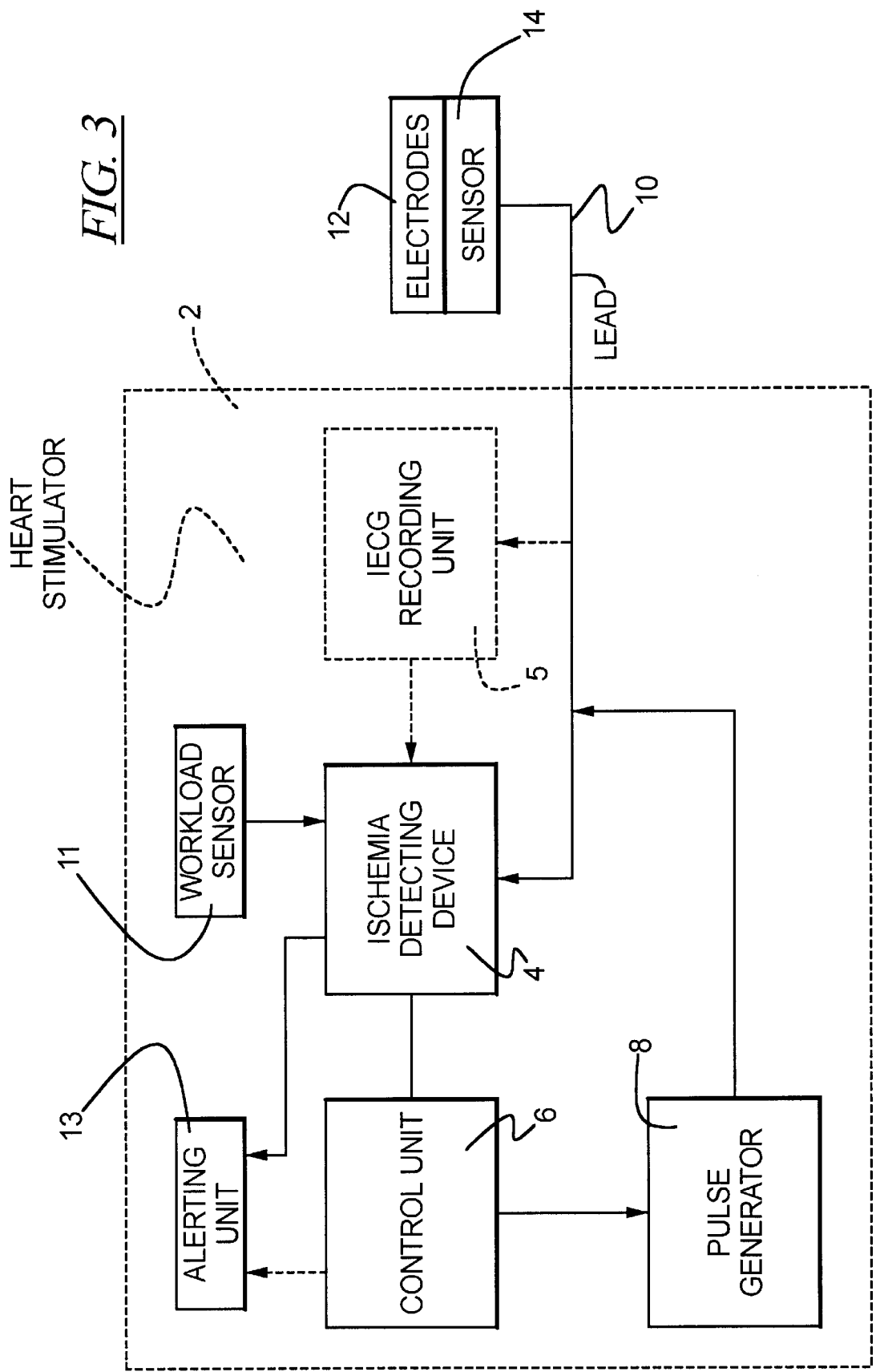
FIG. 3 is a simplified block diagram of one embodiment of the heart stimulator according to the invention.

FIG. 1 illustrates a workload sensor 40 and a breathing activity sensor 42 disposed for sensing the workload and the breathing activity respectively of a patient 44 and delivering corresponding signals to an averaging unit 46, in which average values during time periods of a predetermined length are formed of the workload and breathing activity signals. These average signal values are supplied to detecting unit 48.

The detecting unit 48 contains a memory 50, in which one or more relations between workload and breathing activity are stored, and a comparator 52, in which the relation obtained between the signals from the averaging unit 46 representing workload and breathing activity is compared to the predetermined relations stored in the memory 50.

When a predetermined relation between the signals from the averaging unit 46 is detected alerting means 54 connected to the comparing means is triggered to indicate the occurrence of ischemia. A heart stimulator 56 is connected to the alerting unit 54 for lowering the stimulation rate in response to the detection of an ischemia, as will be described more in detail below.

An example of the predetermined relation between workload x and breathing activity y stored in the memory 50 is a linear relationship like $$ax+by=c$$

where a, b, and c are constants. However, different kinds of non-linear relations are common too.

An alternative embodiment of the detecting unit is shown in FIG. 2. In this embodiment the detecting unit 58 contains two comparators 60, 62 to which the workload signal and the breathing activity signal respectively are supplied for comparing the signals with predetermined threshold values Ref 1 and Ref 2. The outputs of the comparators 60, 62 are connected to the inputs of an AND-gate 64.

The comparator 60 is arranged to deliver an output signal when the workload signal is below the predetermined workload threshold value Ref 1 and comparator 62 delivers an output signal if the breathing activity signal is above the predetermined breathing activity threshold value Ref 2 and in this case an output signal is obtained from the AND-gate 64 for e.g. activation of ischemia alerting means.

FIG. 3 is a simplified block diagram of an implantable heart stimulator 2 according to the invention. The heart stimulator 2 contains an ischemia detector having an ischemia detecting device 4, and a control unit 6, connected to the ischemia detecting device 4. The control unit 6 is connected to a pulse generator 8 for controlling the rate of generated stimulation pulses. The pulse generator in its turn is connected to a lead 10 provided with electrodes 12 at the distal end portion for delivery of stimulation pulses and for possible electrical measurements, which lead 10 is intended to be implanted into the heart of a patient, preferably with the electrodes in the right ventricle, cf. FIG. 4. A sensor 14 is also provided at the distal end portion of the lead 10 and sensed signals are supplied to the ischemia detecting device 4 through the lead 10.

A workload sensor 11 in the form of e.g. an accelerometer for sensing body movements of the patient or a sensor for sensing muscular sounds of the patient is also provided in the heart stimulator 2. For detecting muscular sounds the stimulator case can be used as a microphone and the associated electronics for recording the oscillations of the wall of the case can be glued onto the inner side of the case wall.

The sensor 14 can be used for recording IECGs and has electrodes as described in connection with FIG. 4. The signals are supplied by the lead 10 to an IECG recording unit 5. The IECG recording unit 5 comprises a sensor for sensing the IECG baseline offset and determining the breathing activity from this baseline offset. The baseline offset is preferably measured on a small DC bias voltage. An output signal from the IECG recording unit 5 is delivered to the ischemia detecting device 4.

The DC bias voltage is supplied during a fraction of the breathing cycle and at certain defined positions of the cardiac cycle.

The heart stimulator 2 is also provided with alerting unit 13, e.g. of a wrist watches "beeper-type".

These alerting unit 13 is connected to the ischemia detecting means 4 to be activated by a detected ischemia. Alternatively the alerting means can be connected to the control unit 6 to be activated when the stimulation rate is lowered. This is of value for patients having a "silent" ischemia, the occurrence of which the patient would otherwise not be aware of.

Figure 4:
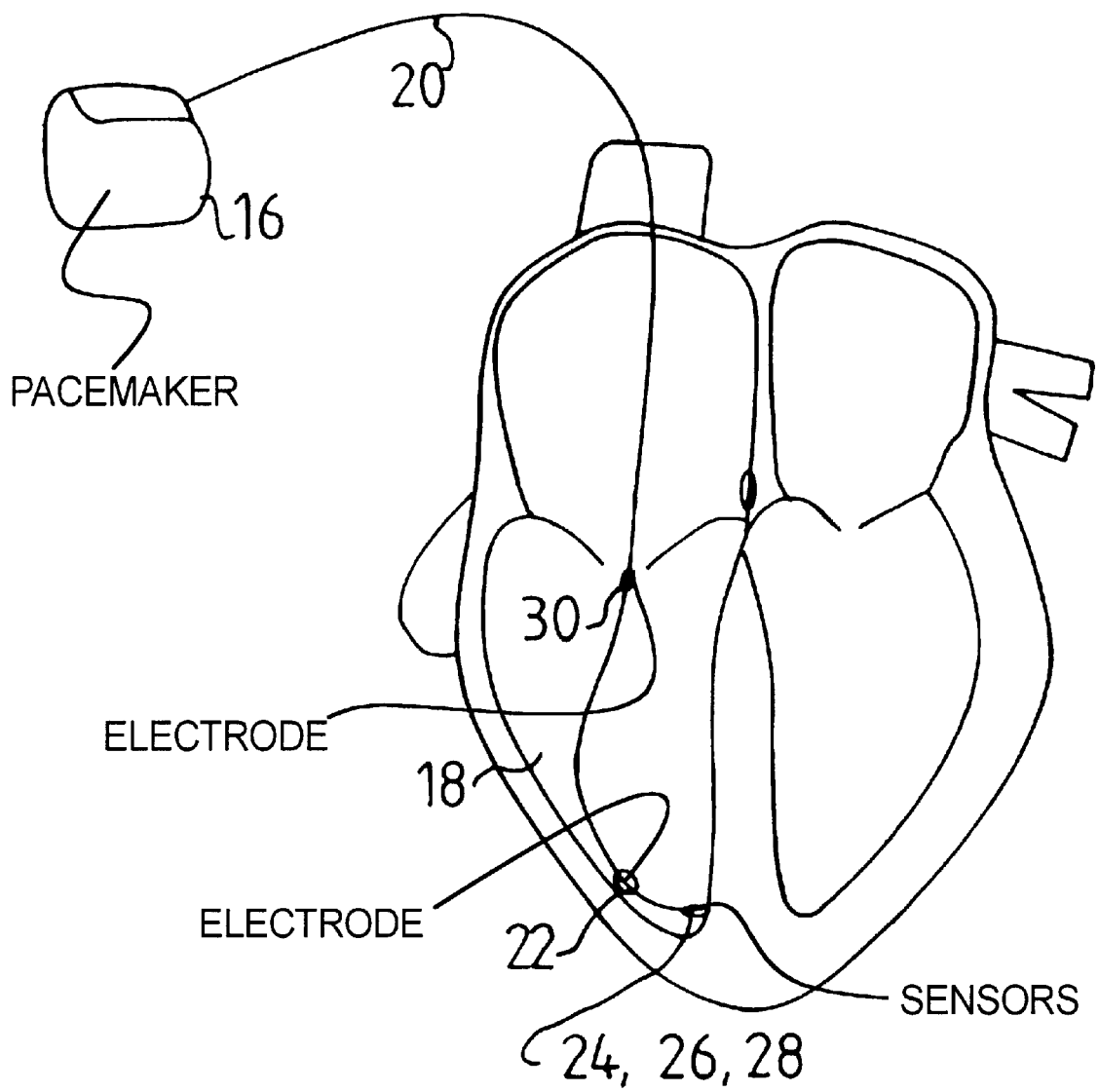
FIG. 4 shows a pacemaker as shown in FIG. 3 with its lead implanted in the right ventricle of the heart.

FIG. 4 shows an implanted heart stimulator in the form of a pacemaker 16, connected to the right ventricle 18 on the heart of a patient by its lead 20, which is of a bipolar type with an electrode ring 22 and with a tip electrode 24 and sensors 26, 28.

With the heart stimulator according to the invention the stimulation rate is reduced in response to the detection of an ischemia. There are different possibilities of reducing the stimulation rate. The control unit 6 can inhibit the delivery of a particular stimulation pulse thus temporarily producing a longer interval between two consecutive pulses. The control unit 6 can also be arranged to more regularly inhibit a stimulation pulse out of a specified number of stimulation pulses in response to a detected ischemia. The control unit 6 can also be arranged to control the pulse generator such that the stimulation rate is uniformly reduced on the detection of an ischemia, or the stimulation rate can be shifted to selected lower rates.

The breathing activity can be determined by measuring the AC impedance between the two electrodes 22, 24 of the electrode lead 20 or between one of the electrodes 22, 24 and the case of the pacemaker 16.

The electrodes 22, 24 or the sensors 26, 28 can be used for measuring amplitude modulation of sensed cardiac activity for determining the breathing activity from this measured modulation.

Other possibilities of determining the breathing activity of the patient is by using a sensor for sensing breathing sounds in the thorax of the patient or a sensor for sensing lung volume changes.

Also other kinds of workload sensor can be used in the present invention. Thus the workload sensor can be a sensor for sensing pressure waves in body fluids generated by the workload or activity of the patient. The workload sensor alternatively can be a sensor for sensing metabolic changes, like changes in nutrition and oxygen consumption of the patient.

Although modifications and changes may be suggested by those skilled in the art, it is the intension of the inventors to embody within the patent warranted hereon all changes and modifications as reasonably and properly come within the scope of their contribution to the art.

What is claimed is:

1. An ischemia detector comprising:
a workload sensor which emits a workload sensor signal representing a sensed workload of a patient;
a breathing sensor which emits a breathing sensor signal representing breathing activity of a patient;
a detector unit connected to said workload sensor and to said breathing sensor and supplied with said workload sensor signal and said breathing sensor signal, said detector unit identifying a state of ischemia upon an occurrence of a predetermined relation between the sensed workload and the sensed breathing activity, said predetermined relation being a sensed low workload and a simultaneously sensed high breathing activity.

2. An ischemia detector as claimed in claim 1 wherein said predetermined relation is a linear relation between the sensed workload and the sensed breathing is activity.

3. An ischemia detector as claimed in claim 1 wherein said detector unit identifies said state of ischemia when the sensed workload is below a predetermined workload threshold value and the simultaneously sensed breathing activity is above a predetermined breathing threshold value.

4. An ischemia detector as claimed in claim 1 further comprising an averaging unit connected between said workload sensor and said breathing sensor, said averaging unit averaging said workload sensor signal and said breathing sensor signal during a plurality of time periods of respective predetermined lengths, and supplying an averaged workload signal, as said sensed workload to said detector unit and an averaged breathing activity, as said sensed breathing activity to said detector unit.

5. An ischemia detector as claimed in claim 1 wherein said workload sensor comprises an activity sensor which senses body movements of a patient.

6. An ischemia detector as claimed in claim 1 wherein said workload sensor comprises a muscular sound sensor.

7. An ischemia detector as claimed in claim 1 wherein said workload sensor comprises a sensor which senses pressure waves and body fluid.

8. An ischemia detector as claimed in claim 1 wherein said workload sensor comprises a sensor which senses metabolic changes of a patient.

9. An ischemia detector as claimed in claim 8 wherein said workload sensor senses changes in oxygen consumption.

10. An ischemia detector as claimed in claim 8 wherein said workload sensor senses changes in nutrition.

11. An ischemia detector as claimed in claim 1 wherein said breathing sensor comprises a sensor which senses breathing sounds in a thorax of a patient.

12. An ischemia detector as claimed in claim 1 wherein said breathing sensor comprises a sensor which senses lung volume changes in a patient.

13. An ischemia detector as claimed in claim 1 wherein said breathing sensor comprises a sensor which measures an amplitude modulation of cardiac activity.

14. An ischemia detector as claimed in claim 1 further comprising a device for recording an IECG of a patient, said IECG exhibiting a base line offset, and wherein said breathing sensor comprises a sensor which identifies a magnitude of said base line offset as a representation of said breathing activity.

15. An ischemia detector as claimed in claim 14 wherein said breathing sensor measures said base line offset on a small DC bias voltage.

16. An ischemia detector as claimed in claim 15 further comprising means for applying said DC bias voltage during a fraction of a breathing cycle of a patient and at predetermined times within a cardiac cycle.

17. An ischemia detector as claimed in claim 1 further comprising an alerting unit which is activated in response to identification of said state of ischemia by said detector unit.

18. An ischemia detector as claimed in claim 1 wherein said breathing sensor comprises two electrodes disposed spaced from each other on an electrode lead, and measures an AC impedance between said two electrodes.

19. An ischemia detector as claimed in claim 1 further comprising a housing having a conductive portion, and wherein said breathing sensor comprises an electrode on an electrode lead and measures an AC impedance between said electrode and said conductive portion of said housing.

20. An implantable heart stimulator comprising:
an ischemia detector comprising:
a workload sensor which emits a workload sensor signal representing a sensed workload of a patient a breathing sensor which emits a breathing sensor signal representing breathing activity of a patient, a detector unit connected to said workload sensor and to said breathing sensor and supplied with said workload sensor signal and said breathing sensor signal, said detector unit identifying a state of ischemia upon an occurrence of a predetermined relation between the sensed workload and the sensed breathing activity, said predetermined relation being a sensed low workload and a simultaneously sensed high breathing activity;
a pulse generator which emits stimulation pulses for delivery to a patient at a stimulation rate; and
means for varying said stimulation rate dependent on identification of a state of ischemia by said ischemia detector.

* * * * *